United States Patent [19]
Guild et al.

[11] Patent Number: 4,915,356
[45] Date of Patent: Apr. 10, 1990

[54] FLUID VALVE

[76] Inventors: Lloyd V. Guild, 337 Thomas Rd.;
Daniel L. Guild, 345 Thomas Rd.,
both of McMurray, Pa. 15317

[21] Appl. No.: 209,053

[22] Filed: Jun. 20, 1988

[51] Int. Cl.⁴ .................. F16K 31/00; G01N 30/02
[52] U.S. Cl. .............................. 251/340; 251/346;
73/23.1
[58] Field of Search .............. 73/23.1; 251/340, 346;
137/872

[56] References Cited

U.S. PATENT DOCUMENTS

| 1,595,186 | 8/1926 | Gray | 251/112 |
| 3,374,660 | 3/1968 | McKinney et al. | 73/23.1 |
| 3,581,573 | 6/1971 | Purcell | 73/23.1 |

Primary Examiner—A. Michael Chambers
Attorney, Agent, or Firm—Parmelee, Miller, Welsh & Kratz

[57] ABSTRACT

A fluid valve permits small quantities of fluid from a container to be withdrawn with a syringe. The valve has a sleeve mounted on a hollow stem in fluid flow communication with the container. A septum is movably mounted between the bore of the sleeve and the bore of the stem. The septum has a first surface facing into the hollow stem and a second aligned surface facing the atmosphere around the valve. A needle is inserted through the aligned surfaces of the septum to withdraw fluid in the stem bore or in the container and is then withdrawn.

7 Claims, 1 Drawing Sheet

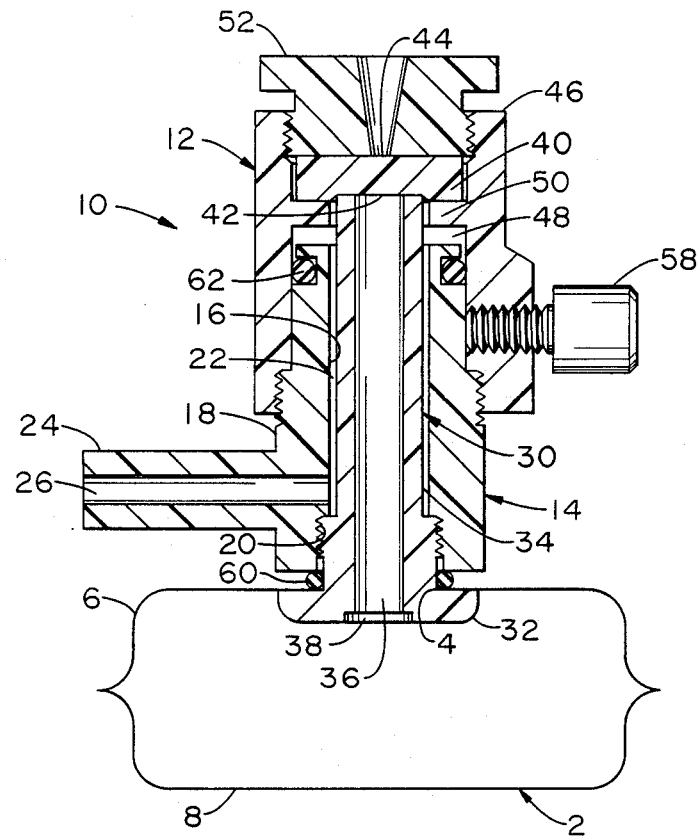

FLUID VALVE

This invention relates to fluid valves for controlling the flow of fluids into and out of containers such as bags, bottles and the like. It is particularly useful in pollution and hygiene studies for collecting samples of a flowing or static body of fluid into a bag for later analysis. For example, samples of various gaseous and liquid streams in industrial processes and discharges into the general environment are commonly pumped through a valve in a line connected to a sampling bag and collected in the bag. The bag is normally taken to another location such as a laboratory for analysis where, for example, the in-line valve is then opened to take some of the fluid for analysis. In the case of gases, the sample is generally analyzed by gas chromotography and only very small sample quantities are needed for each test. However, as in the case of gas chromotography, large amounts of samples are wasted and may contaminate the laboratory because the valve capacity is too great. If the valve were sized for small flows, then the sampling bags could not be filled in a reasonable time. Complicated highly designed valves and flow control elements are not useful because the nature of the service will not support the use of costly equipment. However, fluid valves for this service must also be constructed of materials which will not contaminate the sample.

The valve of the present invention permits fluids to be sampled at a reasonable rate and also to be withdrawn from a sampling bag or other container in very small amounts without wasting the sample and contaminating the atmosphere. The valve has a valve body with one of its ends adapted for fluid flow with a container. A flow control element, which is movably supported by the valve body for opening and closing the valve, has a first surface in fluid flow communication with the fluid in the container and a second surface which does not communicate with fluid in the valve body. The second surface is aligned with the first surface and is disposed in communication with the atmosphere around the valve. Fluid samples to be analyzed may be obtained either in the conventional manner by merely opening the valve or economically and conveniently by inserting a commonly used syringe through the two surfaces of the flow control element. Preferably the control element will tend to close the puncture hole after the needle is withdrawn. In addition, the valve is not structurally complicated and may be readily fabricated from presently used materials at an acceptable cost.

Other details, objects and advantages of the invention will become apparent as the following description of a presently preferred embodiment thereof proceeds.

The accompanying DRAWING shows in cross section a valve 10 embodying the present invention with a commonly used collapsible bag 2. The assembly may be constructed by installing the valve 10 in a hole 4 of sheet 6 and then sealing the edges of the sheet 6 with the edges of a second sheet 8. The valve 10 and the bag 2 may be directly connected (as is shown in the DRAWING) or may be indirectly connected by a length of tubing or the like for fluid flow communication between them. Containers such as bottles may be alternatively used in place of bags 2. Containers should be made of stainless steel, or unplasticized polypropylene, polyethylene, teflon, tedlar or other material which will not contaminate the sample.

The valve 10 has a valve body 12 generally comprised of a sleeve 14 having a bore 16 defined by the sleeve wall 18 fastened through internal threads 20 to a stem 30 extending out of the container 2 and through the bore 16. A passageway 22 for the flow of fluid is formed in the bore 16 by the clearance between the tube wall 18 and the stem 30. An O-ring 60 provides a fluid tight seal between the sleeve 14 and the stem 30 and also between the bag 2 and a flange 32 of the stem 30. A side arm 24 extends from the tube wall 18 with a bore 26 extending through the arm 24 to the passageway 22.

The stem 30 has a sleeve wall 34 extending from the flange 32 with a bore 36 through them in fluid flow communication with the passageway 22 and the bag 2. The flange 32 may have a cross channel 38 extending from an edge across the sleeve bore 36 to another edge which permits fluid to fill a collapsed bag with sheet 8 otherwise sealing off the bore 36.

A flow control element such as a septum 40 controls the flow of fluid between the passageway 22 and the stem bore 36. The septum 40 has a first surface 42 which faces into the stem bore 36 and a second surface 44 which is aligned with the first surface 42 and communicates with the atmosphere around the valve 10. The septum 40 is supported about the periphery of its first surface 42 in the bore 48 of a collar 46 on a shoulder 50 extending into the bore 48. Preferably the shoulder 50 is a flange continuously supporting the septum 40 about its first surface 42. A cap 52 is disposed adjacent to the septum surface 44 facing the atmosphere and threadably engages the collar 46 for firmly holding the septum 40 against the shoulder 50. The cap 52 has an internal surface defining a hole aligned with the first septum surface 42 which faces the stem bore 36. As shown in the drawing the hole preferably is tapered and extends across the entire cross-section of the cap 52 so that a small portion of the septum surface 44 which faces the atmosphere around the valve also communicates with the atmosphere.

The collar 46 is threadably fastened to the sleeve 14 for moving the septum 40 toward and away from the stem 30 for closing and opening the valve 10. A set screw 58 locks the collar 46 in place. An O-ring 62 provides a fluid seal between the sleeve 14 and the collar 46.

The valve 10 is generally comprised of commonly used plastic, stainless steel or other materials which do not contaminate the sample. The valve body may be made from such materials as ABS, high density polypropylene, stainless steel or the like. The septum is preferably an elastomer such as rubber or silicone faced with teflon or tedlar toward stem 34.

In use, the side arm of a valve attached to a collapsed bag is connected to a sample connection on a processing line or vessel by flexible tubing or other suitable means. The collar 46 is rotated to move the septum 40 away from the stem 30 so that a sample of the fluid will flow through the valve 10 and fill the bag 2. The collar 46 is then rotated in the reverse direction to close the septum 40 on the stem 14. The tubing is disconnected from the valve 10 and the sample is taken to a laboratory or another site for testing. Small quantities of the sample may be withdrawn from a closed valve 10 by puncturing the aligned first and second surface of the septum with a hypodermic needle. A tapered hole in a cap 52 extending to the septum surface 44 permits the needle to be easily aligned with the stem bore 36 and provides maximum reinforcing support for the punctured septum 14. Preferably, the septum 14 is an elastomer and will tend to seal the small puncture hole after the needle is withdrawn.

While a presently preferred embodiment of the present invention has been shown and described, it is to be distinctly understood that the invention is not limited thereto but may be otherwise embodied within the scope of the following claims.

We claim:

1. A fluid valve comprising a valve body having an end adapted to be in fluid flow communication with a container, and a flow control element movably supported by the valve body for controlling fluid flow through the valve body, the flow control element having a first surface in communication with the fluid in the container and a second surface which does not communicate with fluid in the valve body when the flow control element is controlling fluid flow through the valve body and is aligned with the first surface, the second surface disposed in communication with the atmosphere around the valve.

2. The valve of claim 1 wherein the flow control element is an elastimer.

3. A fluid valve for collecting fluid samples in a container comprising: a valve body comprising a sleeve having a bore mounted on a stem having a bore within the sleeve bore, the sleeve bore adapted to be in fluid flow communication with a body of fluid and the stem bore adapted to be in fluid flow communication with the container, with a passageway in the sleeve bore defined by the sleeve and the stem, the passageway and the stem bore comprising a channel for the fluid samples to flow; a septum movably mounted on the valve body and disposed between the passageway and the stem bore for controlling the flow of fluid samples through the valve body, the septum having a first surface facing into the stem bore and having a second surface aligned with the first surface and facing toward the atmosphere around the valve.

4. The valve of claim 3 further comprising a collar with a bore and a shoulder extending into the bore, the collar movably mounted on the valve body, the shoulder supporting the septum about the periphery of the first septum surface, and a cap fastened to the collar and disposed adjacent to the second septum surface.

5. The valve of claim 4 wherein the cap has an internal surface defining a hole aligned with the first septum surface.

6. The valve of claim 5 wherein the internal surface defines a tapered hole which exposes a portion of the second septum surface to the atmosphere.

7. The valve of claim 3 wherein the septum is comprised of an elastimer.

* * * * *